US007611870B2

(12) United States Patent
Feinberg

(10) Patent No.: US 7,611,870 B2
(45) Date of Patent: Nov. 3, 2009

(54) METHODS FOR IDENTIFYING CANCER RISK

(75) Inventor: Andrew P. Feinberg, Lutherville, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 322 days.

(21) Appl. No.: 10/336,552

(22) Filed: Jan. 3, 2003

(65) Prior Publication Data

US 2004/0002082 A1 Jan. 1, 2004

Related U.S. Application Data

(60) Provisional application No. 60/391,810, filed on Jun. 27, 2002.

(51) Int. Cl.
C12P 19/34 (2006.01)
C12Q 1/68 (2006.01)
C07H 21/02 (2006.01)
C07H 21/04 (2006.01)

(52) U.S. Cl. .................. 435/91.2; 435/6; 536/23.1; 536/24.3; 536/24.33

(58) Field of Classification Search ................ None
See application file for complete search history.

(56) References Cited

U.S. PATENT DOCUMENTS 5,552,277 A 9/1996 Nelson et al.
5,786,146 A 7/1998 Herman et al.
6,235,474 B1 * 5/2001 Feinberg ................... 435/6

FOREIGN PATENT DOCUMENTS

WO WO 2004/010850 2/2004

OTHER PUBLICATIONS

Feinberg et al., "The history of cancer epigenetics", Nature Reviews Cancer, vol. 4, pp. 1-11, Feb. 2004.*
Ransohoff et al., "Developing molecular markers for cancer", Science, vol. 299, pp. 1679-1680, Mar. 2003.*
Ohlsson, "Loss of IGF2 imprinting: mechanisms and consequences", Novartis Found. Symp., vol. 262, pp. 108-121, 2004.*
Jirtle, "IGF2 loss of imprinting: a potential heritable risk factor", Gastroenterology, vol. 126, pp. 1190-1193, Apr. 2004.*
Woodson et al., "Loss of insulin-like growth factor-II imprinting and the presence of screen-detected colorectal adenomas in women", Journal of the National Cancer Institute, vol. 96, pp. 407-410, Mar. 2004.*
Kaneda et al., "Loss of imprinting of IGF2: a common epigenetic modifier of intestinal tumor risk", Cancer Research, vol. 65, pp. 11236-11240, Dec. 2005.*
Khoury et al., "Population screening in the age of genomic medicine", New England Journal of Medicine, vol. 348, pp. 50-58, Jan. 2003.*

Cruz-Correa et al., "Loss of imprinting of the IGF2 gene is a diffuse colorectal molecular abnormality which may predict colorectal cancer risk", Gastroenterology, vol. 122, No. 4, Suppl. 1, p. A-33, Apr. 2002.*
Cruz-Correa et al., "Loss of imprinting of the IGF2 gene is a diffuse colorectal molecular abnormality that may predict colorectal cancer risk", Journal of Investigative Medicine, vol. 50, No. 2, p. 161A, Mar. 2002.*
Cui et al., "Loss of imprinting in normal tissue of colorectal cancer patients with microsatellite instability", Nature Medicine, vol. 4, No. 11, pp. 1276-1280, Nov. 1998.*
Cui et al., "Loss of IGF2 imprinting: a potential marker of colorectal cancer risk", Science, vol. 299, pp. 1753-1755, Mar. 14, 2003.*
Fletcher, "Screening colonoscopy: option of preference?", Gastrointestinal Endoscopy, vol. 51, No. 5, pp. 624-627, 2000.*
Reik et al., "IGF2 imprinting in development and disease", International Journal of Developmental Biology, vol. 44, pp. 145-150, 2000.*
Fukuzawa et al., "Epigenetic differences between Wilms' tumors in white and east-Asian children", The Lancet, vol. 363, pp. 446-451, Feb. 2004.*
Ravenel, J.D., et al., *J. Natl. Cancer Inst.* vol. 93, 2001, pp. 1698-1703.
Rainer et al., *Nature*, vol. 362, 1993, pp. 747-749.
Feinberg, A.P. and Vogelstein, B., "Hypomethylation Distinguishes Genes of Some Human Cancers From Their Normal Counterparts," *Nature* (Lond.), vol. 301, 1983, pp. 89-92.
Feinberg, A.P., et al. "Reduced Genomic 5-Methylcytosine Content in Human Colonic Neoplasia," *Cancer Res.*, vol. 48, 1988, pp. 1159-1161.
Ogawa, O., et al., "Relaxation of Insulin-Like Growth Factor II Gene Imprinting Implicated in Wilm's Tumour," *Nature* (Lond.), vol. 362, 1993, pp. 749-751.
Steenman, M. J., et al., Loss of Imprinting of IGF2 is Linked to Reduced Expression and Abnormal Methylation of H19 in Wilms' Tumour, *Nat. Genet*, vol. 7, 1994, pp. 433-439.
Uegima, H., et al., "Hot-Stop PCR: a Simple and General Assay for Linear Quantitation of Allele Ratios," *Nat. Genet.*, vol. 25, 2000, pp. 375-376.
Sullivan, M.J., et al., "Relaxation of IGF2 Imprinting in Wilms Tumours Associated with Specific Changes in IGF2 Methylation," *Oncogene*, vol. 18, 1999, pp. 7527-7534.
Moore, T, et al., Multiple Imprinted Sense and Antisense Transcripts, Differential Methylation and Tandem Repeats in a Putative Imprinting Control Region Upstream of Mouse $IGF^2$, *Proc. Natl. Acad. Sci. USA*, vol. 94, Nov. 1997, pp. 12509-12514.

(Continued)

*Primary Examiner*—Stephen Kapushoc
(74) *Attorney, Agent, or Firm*—DLA Piper LLP (US)

(57) ABSTRACT

The present invention provides methods and kits for identifying an increased risk of developing cancer in a subject. The methods include analyzing a first biological sample, such as a blood sample, from the subject for loss of imprinting of the IGF2 gene. According to the methods a loss of imprinting is indicative of an increased risk of developing cancer. The method can include analyzing genomic DNA from the sample for altered methylation of the IGF2 gene. The altered methylation for example includes hypomethylation of a differentially methylated region of IGF2, corresponding to SEQ ID NO:1 or a polymorphism thereof. The method can be performed on a subject having no apparent or suspected hyperproliferative disorder such as cancer.

4 Claims, 3 Drawing Sheets

OTHER PUBLICATIONS

Issa, Jean-Pierre J., et al., "Switch from Monoallelic to Biallelic Human *IGF²* Promoter Methylation During Aging and Carcinogenesis." *Proc. Natl. Acad. Sci. USA*, vol. 93, Oct. 1996, pp. 11757-11762.

Nakagawa, H., et al., "Loss of Imprinting of the Insulin-Like Growth Factor II Gene Occurs by Biallelic Methylation in a Core Region of *H19*-Associated CTCF-binding Sites in Colorectal Cancer," *Proc. Natl. Acad. Sci. USA*, Jan. 16, 2001, vol. 98, No. 2, pp. 591-596.

Lee, M.P., et al., "Loss of Imprinting of a Paternally Expressed Transcript, with Antisense Orientation to K,LQT1, Occurs Frequently in Beckwith-Wiedemann Syndrome and is Independent of Insulin-Like Growth Factor II Imprinting," *Proc. Natl. Acad. Sci. USA.*, vol. 96, Apr. 1999, pp. 5203-5208.

Cui, Hengmi, et al., "Loss of Imprinting of *Insulin-like Growth Factor-II* in Wilms' Tumor Commonly Involves Altered Methylation but not Mutations of *CTCF* or Its Binding Site[1]," *Cancer Research*, vol. 61, Jul. 1, 2001, pp. 4947-4950.

Takai, Daiya, et al., "Large Scale Mapping of Methylcytosines in CTCF-binding Sites in the Human *H19* Promoter and Aberrant Hypomethylation in Human Bladder Cancer," *Human Molecular Genetics*, vol. 10, No. 23, 2001, pp. 2619-2626.

Bartolomei, M.S., et al., "Epigenetic Mechanisms Underlying the Imprinting of the Mouse H19 Gene," *Genes & Dev.* 7(9), Sep. 1993, pp. 1663-1673.

Taniguchi, T., et al., "Epigenetic Changes Encompassing the *IGF2/H19* Locus Associated with Relaxation of *IGF2* Imprinting and Silencing of *H19* in Wilms Tumor," *Proc. Natl. Acad. Sci.*, vol. 92, Mar. 1995, pp. 2159-2163.

Catchpoole, D., et al., "Mutation Analysis of *H19* and *NAPlL4* (*hNAP2*) Candidate Gene and *IGF2* DMR2 in Beckwith-Wiedemann Syndrome," *J. Med Genet*, 37(3) Mar. 2000, pp. 212-215.

Nishihara, S., et al., "Multipoint Imprinting Analysis in Sporadic Colorectal Cancers With and Without Microsatellite Instability," *Int. J. Oncol.*, 17(2), Aug. 2000, pp. 317-322.

Hofmann, W.K., et al., "Loss of Genomic Imprinting of Insulin-Like Growth Factor 2 is Strongly Associated with Cellular Proliferation in Normal Hematopietic Cells," *Exp. Hematol*, 30(4), Apr. 2002, pp. 318-323.

Cui, H., et al., "Loss of Imprinting in Colorectal Cancer Linked to Hypomethylation of *H19* and *IGF2*[1]," *Cancer Research*, 62, Nov. 15, 2002, pp. 6442-6446.

Vu, T.H., et al., Symmetric and Asymmetric DNA Methylation in the Human IGF2-H19 Imprinted Region, *Genomics*, 64(2) Mar. 1, 2000, pp. 132-143.

Schoenherr, C.J., et al., "CTCF Maintains Differential Methylation at the *Igf2/H19* Locus," *Nat. Genet*, 33(1), Jan. 2003, pp. 66-69.

Bell, A.C., et al., "The Protein CTCF is Required for the Enhancer Blocking Activity of Vertebrate Insulators," *Cell*, vol. 98, Aug. 6, 1999, pp. 387-396.

Schneider, D. T., et al., "Multipoint Imprinting Analysis Indicates a Common Precursor Cell for Gonadal and Nongonadal Pediatric Germ Cell Tumors[1]," *Cancer Research*, vol. 61, Oct. 1, 2001, pp. 7268-7276.

Uyeno, S., et al., "*IGF2* But not *H19* Shows Loss of Imprinting in Human Glioma[1]," *Cancer Research*, vol. 56, Dec. 1, 1996, pp. 5356-5359.

Yun, K., et al., "Analysis of *IGF2* Gene Imprinting in Breast and Colorectal Cancer by Allele Specific-PCR," *Journal of Pathology*, vol. 187, 1999, pp. 518-522.

Bell, A. C. and Felsenfeld, G., "Methylation of a CTCF—dependent Boundary Controls Imprinted Expression of the Igf2 Gene," *Nature*, vol. 405, pp. 482-485, 2000.

Douc-Rasy, S. et al., "High Incidence of Loss of Heterozygosity and Abnormal Imprinting of H19 and IGF2 Genes in Invasive Cervical Carcinomas. Uncoupling of H19 and IGF2 Expression and Biallelic Hypomethylation of H19," *Oncogene*, vol. 12, pp. 423-430, 1996.

Kaffer, C. R. et al., "A Transcriptional Insulator at the Imprinted H19/Igf2 Locus," *Genes and Development*, vol. 14, pp. 1908-1919, 2000.

Reinhart, B. et al., "Shared Role for Differentially Methylated Domains of Imprinted Genes," *Molecular and Cellular Biol.*, vol. 22, No. 7, pp. 2089-2098, 2002.

Sasaki et al., "Mechanisms of *Igf2/H19* Imprinting: DNA Methylation, Chromatin and Long-Distance Gene Regulation", *Journal of Biochemistry*, 127(5):711-715 (2000).

* cited by examiner

TCTGTTGCACCCTGGACCCAGACTCCTCAATCCACCCAGGGTGGTGTCTGTGG
GGAGGGGGTTCACTTCCCCAGGAAGCACAGCCACGCCGTCCCTCACTGGCCT
CGTCAAGCAGAGCTGTGTGTCCAGTGGCTTTTGCTGGGGCCCCCTCCTTATCT
CCTTCCAAGGTGGGGGTGTTTGGAGGTGGAGGAGGCTTTCATATTCCGTGCC
ATGACCCCTCAAGGCGGGCCATTCGTGTGCACCCTCCACCCCCAGT

FIG. 1

SEQUENCE LISTING

```
<160> NUMBER OF SEQ ID NOS: 5

<210> SEQ ID NO 1
<211> LENGTH: 256
<212> TYPE: DNA
<213> ORGANISM: Homo sapiens

<400> SEQUENCE: 1
tctgttgcac cctggaccca gactcctcaa tccacccagg gtggtgtctg tggggagggg      60
gttcacttcc ccaggaagca cagccacgcc gtccctcact ggcctcgtca agcagagctg     120
tgtgtccagt ggcttttgct ggggcccect ccttatctcc ttccaaggtg ggggtgtttg     180
gaggtggagg aggctttcat attccgtgcc atgacccctc aaggcgggcc attcgtgtgc     240
accctccacc cccagt                                                    256

<210> SEQ ID NO 2
<211> LENGTH: 20
<212> TYPE: DNA
<213> ORGANISM: Artificial sequence
<220> FEATURE:
<223> OTHER INFORMATION: PCR primer

<400> SEQUENCE: 2
ggtgaggatg ggtttttgtt                                                 20

<210> SEQ ID NO 3
<211> LENGTH: 21
<212> TYPE: DNA
<213> ORGANISM: Artificial sequence
<220> FEATURE:
<223> OTHER INFORMATION: PCR primer

<400> SEQUENCE: 3
ctactctccc aacctcccta a                                               21

<210> SEQ ID NO 4
<211> LENGTH: 20
<212> TYPE: DNA
<213> ORGANISM: Artificial sequence
<220> FEATURE:
<223> OTHER INFORMATION: PCR primer

<400> SEQUENCE: 4 attggggtg gagggtgtat                                                  20

<210> SEQ ID NO 5
<211> LENGTH: 21
<212> TYPE: DNA
<213> ORGANISM: Artificial sequence
```

-continued

```
<220> FEATURE:
<223> OTHER INFORMATION: PCR primer

<400> SEQUENCE: 5
tctattacac cctaaaccca a                                           21
```

METHODS FOR IDENTIFYING CANCER RISK

RELATED APPLICATION DATA

This application claims the benefit of priority under 35 U.S.C. § 119(e) of U.S. Ser. No. 60/391,810, filed Jun. 27, 2002, the entire contents of which is incorporated herein by reference.

STATEMENT OF GOVERNMENT SUPPORT

This invention was made in part with government support under Grant No. R01 CA65145 and K07 CA092445 awarded by the National Institutes of Health. The United States government may have certain rights in this invention.

BACKGROUND OF THE INVENTION

1. Field of the Invention

The present invention relates generally to methods for detecting the presence of or risk of developing cancer and more specifically to methods for detecting the presence of hypomethylation of the IGF2 gene.

2. Background Information

The single greatest impediment to cancer diagnosis is the general requirement that the tumor itself must be detected directly. Efforts to identify genetic abnormalities in normal tissues of patients with cancer or at risk of cancer have been disappointing. For example, BRCA1 mutations are present in only about 1% of breast cancers. A small fraction of patients with colorectal cancer have predisposing mutations in the APC gene (>1%), causing adenomatous polyposis coli. An even smaller fraction show mutations in genes responsible for replication error repair (>2% of colon cancer patients, or much less than 1% of the population), show mutations in genes responsible for nucleotide mismatch error repair causing hereditary nonpolyposis colorectal cancer (HNPCC or Lynch syndrome).

Diagnostic methods such as microsatellite instability, require for identification that a patient already have a tumor. For example, microsatellite instability compares microsatellite marker length between the monoclonal tumor cell population and normal tissue derived from the same patient.

Family history still remains the most reliable diagnostic procedure for identifying patients at risk of cancer. A molecular diagnostic approach that might identify patients with cancer or at risk of cancer, using only normal tissue, would offer a decisive advantage for intervention and treatment.

Except for rare hereditary cancer syndromes, the impact of molecular genetics on cancer risk assessment and prevention has been minimal. Cancer surveillance has been effective for some cancers in which risk can be identified, for example colorectal cancer in familial adenomatous polyposis coli and hereditary nonpolyposis colorectal cancer (Markey, L., et al., *Curr. Gastroenterol. Rep.* 4, 404-413 (2002)), but these syndromes cumulatively account for less than 1% of cancer patients (Samowitz, W. S., et al., *Gastroenterology* 121, 830-838 (2001); Percesepe, A., et al., *J. Clin. Oncol.* 19, 3944-3950 (2001)). Nevertheless, genetics is thought to contribute substantially to cancer risk, since the odds ratio for malignancy increases in patients with first degree relatives with cancer, e.g., 2 to 3-fold in colorectal cancer (Fuchs, C. S., et al., *N. Engl. J Med.* 331, 1669-1674 (1994)). Therefore, there remains a need to develop genetic tests to identify these patients.

Accordingly, no tests are available for identifying common cancer risk in the general population. As discussed above, genetic abnormalities that are known to predispose to cancer are rare. At the same time, advances in cancer treatment have had a small impact on morbidity and mortality. A major advance in cancer requires identification of patients at risk (i.e. identifies patients before they develop cancer), which could be combined with increased surveillance and chemoprevention, similar to the modern approach to cardiovascular medicine.

Thus, there remains a need for a diagnostic method for detecting and/or screening for the presence of diseases and/or the risk of developing a disease. In particular, there remains a need for a method for detecting and/or screening for the presence of cancer, which does not require a tumor sample. There also remains a need for a method of detecting and/or screening for the presence of cancer and/or the risk of developing cancer that can be applied to a wide section of the population.

SUMMARY OF THE INVENTION

The present invention meets these and other needs by providing methods and kits that are based on the finding of an association between loss of imprinting (LOI) and family history of colorectal cancer (CRC) and between LOI and present or past personal history of colorectal neoplasia. Accordingly, methods of the present invention analyze LOI, especially LOI of the IGF2 gene, including altered methylation of the IGF2 gene, to identify an increased risk of developing cancer in a subject.

In one embodiment, the present invention relates to a method for identifying an increased risk of developing cancer in a subject. The method includes analyzing a first biological sample from the subject for loss of imprinting of the IGF2 gene. According to the method a loss of imprinting is indicative of an increased risk of developing cancer. The method can include analyzing genomic DNA from the sample for hypermethylation or hypomethylation of the IGF2 gene. In certain embodiments, the method includes analyzing the genomic DNA for hypomethylation of a differentially methylated region of IGF2, corresponding to SEQ ID NO:1 or a polymorphism thereof. The method can be performed during routine clinical care, on a subject having no apparent or suspected hyperproliferative disorder such as cancer. The first biological sample can be a blood sample, for example.

In one aspect, the method can further include analysis of a second biological sample from the subject at a target tissue for loss of imprinting of the IGF2 gene, wherein a loss of imprinting in the second sample is indicative of an increased risk of developing cancer in the target tissue. In certain embodiments, the second biological sample is not a blood sample. For example, the first biological sample can be a blood sample and the second biological sample can be isolated from colorectal tissue. In embodiments where the second biological sample is isolated from colorectal tissue, the cancer is typically colorectal cancer.

In certain aspects, a third biological sample is isolated from colorectal tissue at a time point after the second sample is isolated, and the subject is screened for an increased risk of developing colorectal cancer by analyzing the third biological sample from the subject for loss of imprinting of the IGF2 gene. The timepoint, for example, can be taken at least 2 months after isolation of the second sample. For example, the time point can be an annual time point.

In another embodiment, the present invention provides a method for managing health of a subject. The method includes performing the method discussed above, and then performing a traditional cancer detection method on the subject if the subject has an increased risk for developing cancer. The traditional cancer detection method can be, for example, colonoscopy.

In yet another embodiment, the present invention provides a method for prognosing cancer risk of a subject. The method includes analyzing a first biological sample from the subject for altered methylation of a differentially methylated region (DMR) of the IGF2 gene. The altered methylation can be hypermethylation or hypomethylation. For example, the method can include hypomethylation of a differentially methylated region (DMR) corresponding to SEQ ID NO:1, or a polymorphism thereof. Hypomethylation is indicative of an increased risk of developing cancer. In this aspect of the invention, the first biological sample is typically a blood sample.

In one aspect, the present invention provides a method for identifying predisposition to colorectal cancer of a subject. The method includes identifying a loss of imprinting in a biological sample from the subject and correlating the loss with a predisposition to colorectal cancer. Loss of imprinting is associated with an increased predisposition to colorectal cancer.

In another aspect, the present invention provides a kit for determining a methylation status of a differentially methylated region (DMR) of IGF2 corresponding to SEQ ID NO:1 or a polymorphism thereof. The kit includes an oligonucleotide probe, primer, or primer pair, or combination thereof, capable of binding to the DMR with or without prior bisulfite treatment of the DMR. The kit can include one or more detectable labels.

The kit can also include a plurality of oligonucleotide probes, primers, or primer pairs, or combinations thereof, capable of binding to the DMR with or without prior bisulfite treatment of the DMR. The kit can include an oligonucleotide primer pair that hybridizes under stringent conditions to all or a portion of the DMR only after bisulfite treatment. The kit can include instructions on using kit components to identify an increased risk of developing cancer. In certain embodiments the instructions relate to subjects of the general population.

BRIEF DESCRIPTION OF THE DRAWINGS

FIG. 1 provides the sequence of a differentially methylated region (DMR) of the IGF2 gene. (SEQ ID NO:1). The IGF2 DMR corresponds to residues −566 bp to −311 bp relative to human IGF2 exon 3, which corresponds to positions 661 to 916 of GenBank accession no. Y13633.

DETAILED DESCRIPTION OF THE INVENTION

Figure 2A:
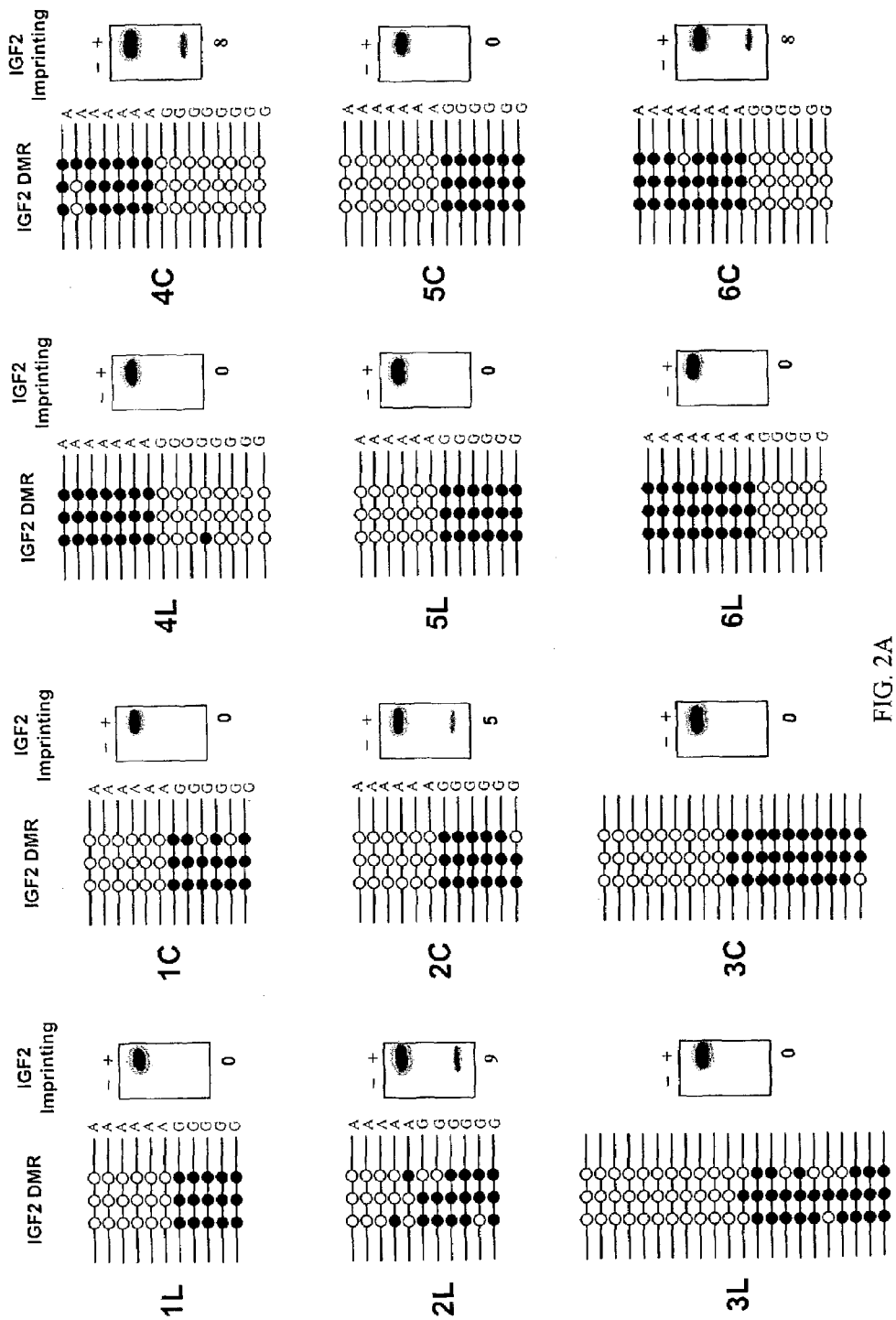
FIGS. 2A and 2B shows methylation status and imprinting analysis of the IGF2 DMR of SEQ ID NO:1, in PBL and normal colonic mucosa with either normal imprinting or LOI of IGF2. (A) IGF2 DMR shows normal methylation in PBL and normal colonic mucosa with normal imprinting of IGF2. Shown are the methylation states of individual PCR products subcloned after bisulfite treatment and PCR. In some cases, individual alleles can be distinguished by single nucleotide polymorphisms on the same PCR product (shown at right). Ten to 20 clones were sequenced depending on heterozygosity at the SNP site. Filled circles represent methylated cytosine and open circles represent unmethylated cytosine. Imprinting analysis was performed by hot-stop PCR (Uejima, H., et al., *Nat. Genet.* 25, 375-376 (2000)), and is shown without (−) and with (+) reverse transcriptase. LOI index is displayed numerically (LOI index=(less active allele/more active allele)×100%). LOI is defined as an LOI index>25 (Cui, H., et al., *Nat. Med.* 4, 1276-1280 (1998)). Patient samples are matched PBL (Patient number includes "L") and colon from the same individuals (Patent number includes "C"). Single nucleotide polymorphisms distinguishing alleles are shown on the left. (B) IGF2 DMR shows biallelic hypomethylation in PBL and normal colonic mucosa with LOI of IGF2, except for one sample that displays partial methylation of both alleles.

Although many conventional genetic mutations have been observed in human cancer, most do not occur at high frequency in the general population. The present invention is based on the finding of an association between loss of imprinting (LOI) and family history of colorectal cancer (CRC) and between LOI and present or past personal history of colorectal neoplasia. Accordingly, methods of the present invention analyze a common molecular marker of cancer risk to identify an increased risk of developing cancer in a subject. In embodiments, the method is a DNA-based blood test for the general population.

As illustrated in the Example section, the present invention provides a prognostic test for cancer risk, especially colorectal cancer risk. The population frequency of the hypomethylation of IGF2 is approximately 8% when the sample is a blood sample. In embodiments involving a second sample isolated from colorectal tissue, an additional 10% of the population are positive. Therefore, the present invention provides methods that identify cancer risk at high frequency in the general population. A positive blood test confers an increased risk of colorectal risk of colorectal cancer, and potentially can be used to identify high risk patients in the general population, for increased cancer surveillance. The method provides an additional advantage in that a negative test excludes patients from repeat colonoscopic examination who may have a positive family history. Furthermore, the test can be performed on RNA or DNA samples.

Accordingly, the present invention relates to a method for identifying an increased risk of developing cancer in a subject. The method includes analyzing a first biological sample from the subject for loss of imprinting of the IGF2 gene. According to the method, a loss of imprinting is indicative of an increased risk of developing cancer.

A method of the present invention can also be used to infer a cancer risk of a subject. As discussed above, the method can include analyzing a first biological sample from the subject for loss of imprinting of the IGF2 gene. According to the method, a level of imprinting is associated with a cancer risk, for example in certain embodiments a loss of imprinting is indicative of an increased risk of developing cancer.

A method of the invention can include analyzing genomic DNA for altered methylation of the IGF2 gene. The method can include analyzing genomic DNA from the sample for hypermethylation or hypomethylation of the IGF2 gene, wherein either hypermethylation or hypomethylation can be associated with an increased risk of developing cancer. Additionally, the altered methylation can occur within either exons or introns. The present disclosure illustrates that changes in methylation of the IGF2 gene can be associated with cancer. An increased risk of developing cancer has been associated with hypermethylation of the H19 DMR. As illustrated in the Example section herein, for the IGF2 gene hypermethylation of the DMR of SEQ ID NO:1 can be associated with an increased risk of developing cancer.

Loss of imprinting, an epigenetic alteration affecting the insulin-like growth factor II gene (IGF2), is found in normal colonic mucosa of approximately 30% of colorectal cancer (CRC) patients, compared to 10% of those without colorectal neoplasia (Cui, H., et al., *Nat. Med.* 4, 1276-1280 (1998)). Therefore, LOI occurs at a relatively high rate in CRC patients and in patients without colorectal neoplasia. Before the present invention, however, it was not known, whether LOI in normal cells identifies patients with a history of, presence of, or positive family history for colorectal neoplasia in a population not selected for colorectal cancer.

In the study provided in the Example section, 11 of 123 (9.0%) of patients with no family history of CRC showed LOI in lymphocytes, compared to 13 of 49 (27%) with a positive family history (adjusted odds ratio 4.41, 95% CI 1.62-12.0, p=0.004). Similarly, 7 of 106 (6.6%) patients without past or present colonic neoplasia showed LOI, compared to 12 of 56 (21%) patients with adenomas, and 5 of 9 (56%) patients with CRC (adjusted odds ratios 4.10 [95% CI 1.30-12.8, p=0.016] and 34.4 [95% CI 6.10-194, p<0.001], respectively). These data support the usefulness and effectiveness of methods of the present invention in identifying an increased risk of developing cancer.

For a blood test of risk assessment to be most practical, a DNA rather than RNA-based test can be used. Accordingly, in certain embodiments, methods of the present invention include analyzing the genomic DNA for hypomethylation of a differentially methylated region (DMR) of IGF2 corresponding to SEQ ID NO:1 a polymorphism of a region of a genome corresponding to SEQ ID NO:1, or a fragment of SEQ ID NO:1 or a polymorphism thereof. As illustrated herein, the vast majority of tissues with LOI (i.e., 11 of 12 tissues analyzed herein) show hypomethylation of IGF2, whereas tissues with normal imprinting show normal methylation of IGF2. Thus, LOI in lymphocytes is linked to hypomethylation of a differentially methylated region of IGF2.

A method according to the present invention can be performed during routine clinical care, for example as part of a general regular checkup, on a subject having no apparent or suspected neoplasm such as cancer. Therefore, the present invention in certain embodiments, provides a screening method for the general population. The methods of the present invention can be performed at a younger age than present cancer screening assays, for example where the method can be performed on a subject under 65, 55, 50, 40, 35, 30, 25, or 20 years of age.

If the biological sample of the subject in question is found to exhibit LOI, for example as the result of hypomethylation of the DMR of IGF2 corresponding to the polynucleotide of SEQ ID NO:1, then that subject is identified as having an increased probability of having cancer. In these embodiments, further diagnostic tests may be carried out to probe for the possibility of cancer being present in the subject. Examples of such further diagnostic tests include, but are not limited to, chest X-ray, carcinoembryonic antigen (CEA) or prostate specific antigen (PSA) level determination, colorectal examination, endoscopic examination, MRI, CAT scanning, or other imaging such as gallium scanning, and barium imaging. Furthermore, the method of the invention can be coincident with routine sigmoidoscopy/colonoscopy of the subject. The method could involve use of a very thin tube, or a digital exam to obtain a colorectal sample.

The method of the present invention, especially when used to detect local LOI, can be repeated at regular intervals. While not wanting to be limited to a particular theory, methods directed to detecting local LOI by analyzing a blood sample for LOI, typically identify germline mutations. Therefore, typically one test is sufficient. However, for methods used to detect local LOI, a third sample can be isolated, for example from colorectal tissue, for example at least 2 months after isolation of the second sample For example, the third sample can be isolated at about 1 year after he second sample was isolated. In fact, the method can be repeated annually, for example at an annual routine physical exam. Using this regular testing, a method of the present invention is used to screen for an increased risk of developing colorectal cancer by a method that includes analyzing the third sample from the subject for loss of imprinting of the IGF2 gene.

Additional diagnostic tests can be performed in the future, even if no cancer is present at the time LOI is detected. For example, if LOI is detected in a biological sample of a subject and indicates an increased risk of contracting cancer, periodic (e.g., every 1 to 12 months) chest X-rays, colorectal examinations, endoscopic examination, MRI, CAT scanning, other imaging such as gallium scanning, and/or barium imaging can be scheduled for that subject. Therefore, in these embodiments, LOI is used as a screening assay to identify subjects for whom more frequent monitoring is justified.

The biological sample can be virtually any biological sample, particularly a sample that contains RNA or DNA from the subject. The biological sample can be a tissue sample which contains 1 to 10,000,000, 1000 to 10,000,000, or 1,000,000 to 10,000,000 somatic cells. However, it is possible to obtain samples that contain smaller numbers of cells, even a single cell in embodiments that utilize an amplification protocol such as PCR. The sample need not contain any intact cells, so long as it contains sufficient biological material (e.g., protein or genetic material, such as RNA or DNA) to assess the presence or absence of LOI of IGF2, such as LOI caused by hypomethylation of IGF2 in the subject.

According to the present invention, the biological or tissue sample can be drawn from any tissue that is susceptible to cancer. For example, the tissue may be obtained by surgery, biopsy, swab, stool, or other collection method. The biological sample for methods of the present invention can be, for example, a sample from colorectal tissue, or in certain embodiments, can be a blood sample, or a fraction of a blood sample such as a peripheral blood lymphocyte (PBL) fraction. Methods for isolating PBLs from whole blood are well known in the art. An example of such a method is provided in the Example section herein. In addition, it is possible to use a blood sample and enrich the small amount of circulating cells from a tissue of interest, e.g., colon, breast, etc. using a method known in the art.

When the method of the present invention provides a method for identifying an increased risk of developing colorectal cancer, a biological sample can be isolated from the colon. Such a tissue sample can be obtained by any of the above described methods, or by the use of a swab or biopsy. In the case of stomach and esophageal cancers, the tissue sample may be obtained by endoscopic biopsy or aspiration, or stool sample or saliva sample. In the case of leukemia, the tissue sample is typically a blood sample.

As disclosed above, the biological sample can be a blood sample. The blood sample can be obtained using methods known in the art, such as finger prick or phlebotomy. Suitably, the blood sample is approximately 0.1 to 20 ml, or alternatively approximately 1 to 15 ml with the volume of blood being approximately 10 ml.

Accordingly, in one embodiment, the identified cancer risk is for colorectal cancer, and the biological sample is a tissue sample obtained from the colon, blood, or a stool sample. In another embodiment, the identified cancer risk is for stomach cancer or esophageal cancer, and the tissue may be obtained by endoscopic biopsy or aspiration, or stool sample or saliva sample. In another embodiment, the identified cancer risk is esophageal cancer, and the tissue is obtained by endoscopic biopsy, aspiration, or oral or saliva sample. In another embodiment, the identified cancer risk is leukemia/lymphoma and the tissue sample is blood.

In the present invention, the subject is typically a human but also can be any mammalian organism, including, but not limited to, a dog, cat, rabbit, cow, bird, rat, horse, pig, or monkey.

As mentioned above, for certain embodiments of the present invention, the method is performed as part of a regular checkup. Therefore, for these methods the subject has not been diagnosed with cancer, and typically for these present embodiments it is not known that a subject has a hyperproliferative disorder, such as a colorectal neoplasm.

Methods of the present invention identify a risk of developing cancer for a subject. A cancer can include, but is not limited to, colorectal cancer, esophageal cancer, stomach cancer, leukemia/lymphoma, lung cancer, prostate cancer, uterine cancer, breast cancer, skin cancer, endocrine cancer, urinary cancer, pancreas cancer, other gastrointestinal cancer, ovarian cancer, cervical cancer, head cancer, neck cancer, and adenomas. In one aspect, the cancer is colorectal cancer.

A hyperproliferative disorder includes, but is not limited to, neoplasms located in the following: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital. Typically, as used herein, the hyperproliferative disorder is a cancer. In certain aspects, the hyperproliferative disorder is colorectal cancer.

The method can further include analysis of a second biological sample from the subject at a target tissue for loss of imprinting of the IGF2 gene, wherein a loss of imprinting in the second sample is indicative of an increased risk of developing cancer in the target tissue. In certain embodiments, the second biological sample is not a blood sample. For example, the first biological sample can be a blood sample and the second biological sample can be isolated from colorectal tissue. In these embodiments analysis of the blood sample can be performed to identify overall risk of developing cancer, whereas the colorectal sample can be analyzed to identify subjects that have an increased risk of developing colorectal cancer.

In another embodiment, the present invention provides a method for managing health of a subject. The method includes performing the method for identifying an increased risk of developing cancer discussed above and performing a traditional cancer detection method. For example a traditional cancer detection method can be performed if the method for identifying cancer risk indicates that the subject is at an increased risk for developing cancer. Many traditional cancer detection methods are known and can be included in this aspect of the invention. The traditional cancer detection method can include, for example, one or more of chest X-ray, carcinoembryonic antigen (CEA) level determination, colorectal examination, endoscopic examination, MRI, CAT scanning, or other imaging such as gallium scanning, and barium imaging, and sigmoidoscopy/colonoscopy, a breast exam, or a prostate specific antigen (PSA) assay.

In another embodiment, the present invention provides a method for prognosing cancer risk of a subject. The method includes analyzing a first biological sample from the subject for altered methylation of the IGF2 gene. The altered methylation can be hypomethylation or hypermethylation. For example, the altered methylation can be hypomethylation of a differentially methylated region (DMR) of IGF2 corresponding to SEQ ID NO:1, or a polymorphism thereof. Hypomethylation is indicative of an increased risk of developing cancer. In this aspect of the invention, the first biological sample is typically a blood sample.

In another aspect, the present invention provides a method for identifying predisposition to colorectal cancer of a subject. The method includes identifying a loss of imprinting in a biological sample from the subject and correlating the loss with a predisposition to colorectal cancer. Loss of imprinting is associated with an increased predisposition to colorectal cancer. The method includes analyzing a first biological sample from the subject for hypomethylation of a differentially methylated region DMR of IGF2 corresponding to SEQ ID NO:1, or a polymorphism thereof. Hypomethylation of this DMR is indicative of an increased risk of developing cancer. In this aspect of the invention, the first biological sample is typically a colorectal sample.

It will be recognized that other altered methylation patterns within other regions of IGF2, or other positions within the identified DMR, can be associated with cancer risk. For example, hypermethylation of certain residues of the IGF2 gene may be identified as associated with cancer risk. The present disclosure combined with known methods can be used to identify the altered methylation patterns of IGF2.

In another embodiment, the present invention provides to a method for screening a subject for cancer. The method includes analyzing a first biological sample from the subject for loss of imprinting of the IGF2 gene. According to the method, a loss of imprinting is indicative of an increased risk of developing cancer. The method can include analyzing genomic DNA from the sample for hypomethylation of the IGF2 gene.

As disclosed herein, methods of the present invention involve analyzing a biological sample for loss of imprinting of IGF2. Genomic imprinting is an epigenetic modification of a specific parental chromosome in the gamete or zygote that leads to monoallelic or differential expression of the two alleles of a gene in somatic cells of the offspring. Imprinting affects various essential cellular and developmental processes, including intercellular signaling, RNA processing, cell cycle control, and promotion or inhibition of cellular division and growth.

Genomic imprinting is a parent of origin-specific gene silencing that is epigenetic in origin, i.e. not involving the DNA sequence per se but methylation and likely other modifications heritable during cell division (Feinberg, A. P., in *The Metabolic and Molecular Bases of Inherited Disease*, C. R. Scriver, et al., Eds. (McGraw-Hill, New York, 2002)). Loss of imprinting (LOI) of IGF2 was first discovered in embryonal tumors of childhood, such as Wilms tumor (WT), but is one of the most common alterations in cancer, including ovarian, lung, liver, and colon (Feinberg, A. P., in *The Metabolic and Molecular Bases of Inherited Disease*, C. R. Scriver, et al., Eds. (McGraw-Hill, New York, 2002)). The consequence of LOI is best understood in WT. Here it serves as a gatekeeper in about half of tumors, especially those that occur with relatively late onset, and leads to increased expression of IGF2 (Ravenel, J. D., et al., *J Natl. Cancer Inst.* 93, 1698-1703 (2001)), an important autocrine growth factor in a wide variety of cancers including CRC (Lahm, H., et al., *Br. J. Cancer* 65, 341-346 (1992); M. C. Gelato and J. Vassalotti, *J. Clin. Endocrinol. Metab.* 71, 1168-1174 (1990); El-Badry, O. M., et al., *Cell Growth Diff.* 1, 325-331 (1990); Yee, D., et al., *Cancer Res.* 48, 6691-6696 (1988); Lamonerie, T., et al., *Int. J. Cancer* 61, 587-592 (1995); and Pommier, G. J., et al., *Cancer Res.* 52, 3182-3188 (1992)).

Loss of imprinting can be caused by hypomethylation or hypermethylation of a gene. As such, the present invention includes methods wherein loss of imprinting is identified by hypomethylation or hypermethylation of the IGF2 gene. For example, the loss of imprinting can be the result of hypomethylation of a DMR within the IGF2 gene, corresponding to SEQ ID NO:1, particularly positions 87, 90, and 106 within SEQ ID NO:1.

Methods for detecting loss of imprinting are typically quantitative methods for analyzing imprinting status. The presence or absence of LOI may be detected by examining any condition, state, or phenomenon which causes LOI or is the result of LOI. Such conditions, states, and phenomena include, but are not limited to:

1. Causes of LOI, such as the state or condition of the cellular machinery for DNA methylation, the state of the imprinting control region on chromosome 11, the presence of trans-acting modifiers of imprinting, the degree or presence of histone deacetylation;
2. State of the genomic DNA associated with the genes or gene for which LOI is being assessed, such as the degree of DNA methylation;
3. Effects of LOI, such as:
  a. Relative transcription of the two alleles of the genes or gene for which LOI is being assessed;
  b. Post-transcriptional effects associated with the differential expression of the two alleles of the genes or gene for which LOI is being assessed;
  c. Relative translation of the two alleles of the genes or gene for which LOI is being assessed;
  d. Post-translational effects associated with the differential expression of the two alleles of the genes or gene for which LOI is being assessed;
  e. Other downstream effects of LOI, such as altered gene expression measured at the RNA level, at the splicing level, or at the protein level or post-translational level (i.e., measure one or more of these properties of an imprinted gene's manifestation into various macromolecules); changes in function that could involve, for example, cell cycle, signal transduction, ion channels, membrane potential, cell division, or others (i.e., measure the biological consequences of a specific imprinted gene being normally or not normally imprinted (for example, QT interval of the heart). Another group of macromolecular changes include processes associated with LOI such as histone acetylation, histone deacetylation, or RNA splicing.

When detecting the presence or absence of LOI by relying on any one of these conditions, states, or phenomena, it is possible to use a number of different specific analytical techniques. In particular, it is possible to use any of the methods for determining the pattern of imprinting known in the art. It is recognized that the methods may vary depending on the gene to be analyzed.

Conditions, states, and phenomena which may cause LOI and may be examined to assess the presence or absence of LOI include the state or condition of the cellular machinery for DNA methylation, the state of the imprinting control region on chromosome 11, the presence of trans-acting modifiers of imprinting, the degree or presence of histone deacetylation or histone deacetylation, imprinting control center, transacting modulatory factors, changes in chromatin caused by polycomb-like proteins, trithorax-like proteins, human homologues of other chromatin-affecting proteins in other species such as Su(var) proteins in Drosophila, SIR proteins in yeast, mating type silencing in yeast, or XIST-like genes in mammals.

It is also possible to detect LOI by examining the DNA associated with the gene or genes for which the presence or absence of LOI is being assessed. By the term "the DNA associated with the gene or genes for which the presence or absence of LOI is being assessed" it is meant the gene, the DNA near the gene, or the DNA at some distance from the gene (as much as a megabase or more away, e.g., methylation changes can be that far away, since they act on chromatin over long distances). Typically, for the present invention LOI is identified or analyzed or detected by detecting hypomethylation of a DMR of the IGF2 gene, as described herein.

The degree of methylation in the DNA, associated with the gene or genes for which the presence or absence of LOI is being assessed, may be measured by means of a number of analytical techniques. One method as discussed above, detects loss of imprinting by detecting hypomethylation of a DMR of the IGF2 gene, corresponding to SEQ ID NO:1. In one embodiment, the IGF2 DMR is located at position −566 bp to −311 bp (SEQ ID NO:1) relative to exon 3 of IGF2, (i.e., positions 661 to 916 of GenBank accession no. Y13633) or a polymorphism thereof, or a fragment thereof.

Numerous methods for analyzing methylation status of a gene are known in the art and can be used in the methods of the present invention to identify either hypomethylation or hypermethylation of the IGF2 gene. As illustrated in the Examples herein, analysis of methylation can be performed by bisulfite genomic sequencing. Accordingly, denatured genomic DNA can be treated with freshly prepared bisulfite solution at 55° C. in the dark overnight, followed by column purification and NaOH treatment. Bisulfite treatment modifies DNA converting unmethylated, but not methylated, cytosines to uracil. Treated DNA can be amplified by PCR, using primers 5'-GGTGAGGATGGGTTTTTGTT-3' (SEQ ID NO:2) and 5'-CTACTCTCCCAACCTCCCTAA-3' (SEQ ID NO:3), annealing at 55° C., followed by nested PCR using primers 5'-ATTGGGGGTGGAGGGTGTAT-3' (SEQ ID NO:4) and 5'-TCTATTACACCCTAAACCCAA-3' (SEQ ID NO:5), annealing at 52° C. The other conditions are as described previously (Cui, H., et al., *Nat. Med.* 4, 1276-1280 (1998)).

Bisulfite treatment can be carried out using the CpG Genome DNA Modification kit (Intergen, Purchase, N.Y.) with the following modifications of the manufacturer's protocol: denatured genomic DNA (4 μg) can be incubated at 55° C. in the dark overnight in 1100 μl of freshly prepared Reagent I, with subsequent column purification with the QIAquick PCR purification kit (Qiagen). Purified DNA can be treated at 37° C. for 15 min with freshly prepared 3 M NaOH to a final concentration of 0.3 M NaOH. Then the DNA can be precipitated with ethanol and dissolved in 40 μl of 10 mM Tris (pH 8)–1 mM EDTA for nested PCR. PCR products were purified on 2% agarose gels for direct sequencing as described above. The annealing temperature was 55° C. For sequencing individual clones, the PCR products can be subcloned into a TA Cloning vector (Invitrogen, Carlsbad, Calif.) according to the manufacturer's instructions, and a series of clones, such as 10-15 clones, can be selected for sequencing.

PCR products can be purified using the QIAEX II gel extraction kit (Qiagen) and directly sequenced with an ABI Prism 377 DNA sequencer using the BigDye™ Terminator Cycle Sequencing kit following the manufacturer's protocol (PE Applied Biosystems, Foster City, Calif.).

Altered methylation can be identified by identifying a detectable difference in methylation. For example, hypomethylation can be determined by identifying whether after bisulfite treatment a uracil or a cytosine is present at residues corresponding to position 87, 90, and 106 of SEQ ID NO:1. If uracil is present after bisulfite treatment, then the residue is unmethylated. Hypomethylation is present when there is a measurable decrease in methylation, for example a measurable decrease in methylation of residues corresponding to position 87, 90, and 106 of SEQ ID NO:1, as illustrated in the Example section herein.

In an alternative embodiment, the method for analyzing methylation of the DMR can include amplification using a primer pair specific for methylated residues within a DMR of the IGF2 gene, typically for the present invention, the DMR corresponding to SEQ ID NO:1 or a fragment thereof, or a polymorphism of the DMR corresponding SEQ ID NO:1 or a fragment thereof. In these embodiments, selective hybridization or binding of at least one of the primers is dependent on the methylation state of the target DNA sequence (Herman et al., *Proc. Natl. Acad. Sci. USA*, 93:9821 (1996)). For example, the amplification reaction can be preceded by bisulfite treatment, and the primers can selectively hybridize to target sequences in a manner that is dependent on bisulfite treatment. For example, one primer can selectively bind to a target sequence only when one or more base of the target sequence is altered by bisulfite treatment, thereby being specific for a methylated target sequence.

Other methods are known in the art for determining methylation status of a gene, such as the IGF2 gene, including, but not limited to, array-based methylation analysis and Southern blot analysis.

Methods using an amplification reaction, for example methods above for detecting hypomethylation of the IGF2 DMR corresponding to SEQ ID NO:1, can utilize a real-time detection amplification procedure. For example, the method can utilize molecular beacon technology (Tyagi S., et al., *Nature Biotechnology*, 14: 303 (1996)) or Taqman™ technology (Holland, P. M., et al., *Proc. Natl. Acad. Sci. USA*, 88:7276 (1991)).

Also methyl light (Trinh B N, Long T I, Laird P W. DNA methylation analysis by MethyLight technology, Methods, 25(4):456-62 (2001), incorporated herein in its entirety by reference), Methyl Heavy (Epigenomics, Berlin, Germany), or SNuPE (single nucleotide primer extension) (See e.g., Watson D., et al., *Genet Res.* 75(3):269-74 (2000)). Can be used in the methods of the present invention related to identifying altered methylation of IGF2.

As used herein, the term "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

The present invention can include performing more than one assay for detecting LOI of the IGF2 gene. For example, a method for detecting LOI by detecting hypomethylation of a DMR of the IGF2 gene corresponding to SEQ ID NO:1 can be performed along with methods that analyze expression of alleles that are affected by imprinting to increase the accuracy and/or sensitivity of the assay.

Methods of the present invention can, for example, involve analyzing genomic DNA for hypomethylation of a core sequence within SEQ ID NO:1. Sequences present on a genome, typically the human genome, within the portion of the IGF2 gene corresponding to SEQ ID NO:1, likely will show variable alteration, as found near the H19 and other DMRs in development (Davis, T. L., et al., *Hum. Mol. Genet* 9, 2885-2894 (2000)). In view of the present disclosure, an ordinary artisan can use standard techniques to identify a core sequence within SEQ ID NO:1 for hypomethylation. For example, the amplification product of the amplification reaction disclosed above, can be sequenced with and without bisulfite treatment. An analysis of the sequence will reveal the individual residues that are methylated. As another example, a series of primers can be constructed that selectively hybridize to a series of target sequences within SEQ ID NO:1, in a manner that depends on the methylation state of the target sequence before bisulfite treatment.

The degree of methylation in the DNA associated with the gene or genes for which the presence or absence of LOI is being assessed, may be measured by fluorescent in situ hybridization (FISH) by means of probes which identify and differentiate between genomic DNAs, associated with the gene for which the presence or absence of LOI is being assessed, which exhibit different degrees of DNA methylation. FISH is described in the Human chromosomes: principles and techniques (Editors, Ram S. Verma, Arvind Babu Verma, Ram S.) 2nd ed., New York: McGraw-Hill, 1995, and de Capoa A., Di Leandro M., Grappelli C., Menendez F., Poggesi I., Giancotti P., Marotta, M. R., Spano A., Rocchi M., Archidiacono N., Niveleau A. Computer-assisted analysis of methylation status of individual interphase nuclei in human cultured cells. *Cytometry.* 31:85-92, 1998 which is incorporated herein by reference. In this case, the biological sample will typically be any which contains sufficient whole cells or nuclei to perform short term culture. Usually, the sample will be a tissue sample that contains 10 to 10,000, or, for example, 100 to 10,000, whole somatic cells.

Additionally, as mentioned above, methyl light, methyl heavy, and array-based methylation analysis can be performed, by using bisulfite treated DNA that is then PCR-amplified, against microarrays of oligonucleotide target sequences with the various forms corresponding to unmethylated and methylated DNA.

As mentioned above, methods for detecting LOI can identify altered methylation patterns. However, other methods for detecting LOI are known. For example, certain methods for detecting LOI identify allele-specific gene expression and rely upon the differential transcription of the two alleles. For these methods, RNA is reverse transcribed with reverse transcriptase, and then PCR is performed with PCR primers that span a site within an exon where that site is polymorphic (i.e., normally variable in the population), and this analysis is performed on an individual that is heterozygous (i.e., informative) for the polymorphism. A number of detection schemes can be used to determine whether one or both alleles is expressed. See also, Rainier et al. (1993) *Nature* 362:747-749; which teaches the assessment of allele-specific expression of IGF2 and H19 by reverse transcribing RNA and amplifying cDNA by PCR using new primers that permit a single round rather than nested PCR; Matsuoka et al. (1996) *Proc. Natl. Acad Sci USA* 93:3026-3030 which teaches the identification of a transcribed polymorphism in p57$^{KIP2}$; Thompson et al. (1996) *Cancer Research* 56:5723-5727 which teaches determination of mRNA levels by RPA and RT-PCR analysis of allele-specific expression of p57$^{KIP2}$; and Lee et al. (1997) *Nature Genet.* 15:181185 which teaches RT-PCR SSCP analysis of two polymorphic sites. Such disclosures are herein incorporated by reference. In this case, the biological sample will be any which contains sufficient RNA to permit amplification and subsequent reverse transcription followed by polymerase chain reaction. Typically, the biological sample will be a tissue sample which contains 1 to 10,000,000, 1000 to 10,000,000, or 1,000,000 to 10,000,000, somatic cells.

Quantitative analysis of IGF2 imprinting status can be performed by Hot-stop PCR on cDNA (Uejima, H., et al., *Nat. Genet.* 25, 375-376 (2000)), as illustrated in the Example section herein. LOI index can be calculated by quantitating the PCR product of a less active allele, or a more active allele, ×100%. LOI can be defined as an LOI index greater than 25 (Cui, H., et al., *Nat. Med.* 4, 1276-1280 (1998)). In certain embodiments, methods of the present invention that analyze LOI are performed in subjects that are informative for either an APAI or CA repeat polymorphism within exon 9 of IGF2 (Cui, H., et al., *Cancer Research* 62, 6442-6 (2002)).

Methods that detect hypomethylation or hypermethylation have the advantage over some other LOI assays in that they are not restricted to subjects with imprinted polymorphisms that have altered transcription levels.

It is also possible to utilize allele specific RNA-associated in situ hybridization (ASISH) to detect the presence or absence of LOI by relying upon the differential transcription of the two alleles. In ASISH, the relative abundance of transcribed mRNA for two alleles is assessed by means of probes which identify and differentiate between the mRNA transcribed from the two alleles. Typically, the probes are tagged with fluorescent labels which results in a high sensitivity and easily quantifiable results. ASISH is described in Adam et al. (1996) "Allele-specific in situ hybridization (ASISH) analysis: a novel technique which resolves differential allelic usage of H19 within the same cell lineage during human placental development," *Development* 122:83-47, which is incorporated herein by reference. In this case, the biological sample will typically be any which contains sufficient whole cells or nuclei to perform histological section and in situ hybridization. Usually, the sample will be a tissue sample which contains for example, 10-100,000, or 100-1000, whole somatic cells.

According to the present invention, it is also possible to detect LOI by examining allele-specific post-transcriptional effects (i.e., effects after transcription and before translation), like alternate splicing that depends on which allele was transcribed, and detection of secondary structure of the RNA.

It is also possible, according to the present invention, to detect LOI by examining the relative translation of the two alleles of the gene or genes for which the presence or absence of LOI is being measured. In this case, the presence or relative abundance of the two polypeptides arising from the expression of the two alleles is measured directly. This approach can be effected by any known technique for detecting or quantifying the presence of a polypeptide in a biological sample. For example, allele-specific translational effects may be examined by quantifying the proteins expressed by the two alleles using antibodies specific for each allele (transcribed, translated polymorphism). Such effects may be measured and/or detected by such analytical techniques as Western blotting, or use of an ELISA assay. In this case, the biological sample will be any which contains a sufficient amount of the polypeptide(s) encoded by the gene(s) for which the presence or absence of LOI is being measured.

LOI may also be detected by examining post-translational effects, such as secondary modifications that are specific to one allele, like glycosylation or phosphorylation. For example, one allele may be modified, say by phosphorylation or glycosylation, and the other one not. Because the polymorphism encodes a recognition motif, then one can readily distinguish the difference by a Western blot, detecting alternate migration of the polypeptide or protein; use of antibodies specific for the modified form; radioactive incorporation of phosphoryl group or glycosyl group or other modification (i.e., in living cells, followed by the detection of a band at a varying location).

LOI may also be detected by reliance on other allele-specific downstream effects. For example, depending on the metabolic pathway in which lies the product of the imprinted gene; the difference will be 2.times. versus 1.times. (or some number in between) of the product, and therefore the function or a variation in function specific to one of the alleles. For example, for IGF2, increased mitogenic signaling at the IGF1 receptor, increased occupancy of the IGF1 receptor, increased activity at the IGF2 catabolic receptor, decreased apoptosis due to the dose of IGF2; for KvLQT1, change in the length of the QT interval depending on the amount and isoform of protein, or change in electrical potential, or change in activity when the RNA is extracted and introduced into *Xenopus oocytes*.

It is also possible to detect LOI by detecting an associated haplotype, i.e., linked polymorphisms that identify subjects whose genes are prone to LOI.

LOI can be detected by relying on a polymorphism, i.e., a genetic difference between the two alleles. However, it will be recognized that many of the techniques described above may be used to detect LOI even when there is no polymorphism in the two alleles of the gene or genes for which the presence or absence of LOI is being measured. For example, LOI may be detected by reliance on allele-specific DNA methylation (polymorphism independent); histone acetylation; other modifications to DNA; or alterations in replication timing, when the imprinted allele shows "replication timing asynchrony" i.e. the two alleles replicate at different times. When the two alleles replicate at the same time, LOI may be detected by FISH. Since imprinted alleles pair in the late S phase, LOI may be detected by the absence of such pairing in the late S as observed by FISH.

On the other hand certain techniques are more conveniently used when there is a polymorphism in the two alleles of the gene or genes for which the presence or absence of LOI is being measured. For example, RT-PCR followed by SSCP (single strand conformational polymorphism) analysis; restriction enzyme digestion analysis followed by electrophoresis or Southern hybridization; or radioisotopic PCR; PCR; allele-specific oligonucleotide hybridization; direct sequencing manually or with an automated sequencer; denaturing gradient gel electrophoresis (DGGE); and many other analytical techniques can be used to detect LOI when relying on a polymorphism.

In another embodiment of the present invention the method involves measuring the degree of LOI such as by measuring the degree of hypomethylation of a DMR for a particular gene or set of genes. In certain embodiments, the method includes measuring the degree of hypomethylation of the DMR of IGF2 gene corresponding to SEQ ID NO:1 or a polymorphism thereof, or a fragment thereof.

As used herein, when hypomethylation is measured, "the degree of LOI" means the percentage of methylation compared to a fully methylated DMR. As used herein, when expression of different polymorphisms is compared, "the degree of LOI" means total expression (as measured by actual expression or transcription) attributable to the allele which is normally imprinted. The degree of LOI may be calculated by allele ratio, i.e., the more abundant allele divided by the less abundant allele. The degree of LOI may be determined by any method which allows the determination of the relative expressions of the two alleles. For example, a degree of LOI of 100% reflects complete LOI (equal expression of both alleles), while a degree of LOI of 0% reflects no LOI (expression of only one allele). Any method of measuring the relative expression of the two alleles is considered to be included in the present invention.

The degree of LOI can be measured for the IGF2 gene when screening for the presence of colorectal cancer, or other cancers, e.g., the degree of LOI is measured for the IFG2 gene when screening for the presence of stomach cancer, esophageal cancer, or leukemia.

The degree of LOI can be measured by measuring the degree of hypomethylation of the DMR of IGF2 corresponding to SEQ ID NO:1 or a fragment thereof, or a polymorphism thereof, in a blood sample, for example a PBL sample, wherein a high degree of hypomethylation is indicative of an increased risk for cancer. For example, a series of genomic clones can be analyzed that are derived from the subject. These clones can be analyzed for hypomethylation of the DMR of IGF2 corresponding to SEQ ID NO:1. The degree of hypomethylation can be determined by identifying the methylation frequency of possibly methylated sites. Possibly methylated sites, are cytosine residues that are typically methylated in a subject, but become unmethylated in certain subjects that are at an increased risk of developing cancer. For example, residues corresponding to positions 87, 90, and 106 of SEQ ID NO:1 can be analyzed in one or a series of genomic clones. If uracil is present after bisulfite treatment, then the residue is unmethylated. Hypomethylation is present when in a series of clones of genomic DNA, there is a measurable decrease in methylation, such as a measurable decrease in methylation of positions 87, 90, and 106 of SEQ ID NO:1.

A linear detection platform can be employed to quantitate LOI. A linear detection platform is a detection platform that allows quantitation because the amount of target present and signal detected are linearly related. In this regard, a PhosphorImager (model 445SI, manufactured by Molecular Dynamics), which detects radioactive emissions directly from a gel, can be used. Other linear detection systems include carefully titrated autoradiography followed by image analysis, beta-emission detection analysis (Betascan). Another linear detection platform is an automated DNA sequencer such as ABI 377 analyzer. Another linear detection platform is an array based system with appropriate software. Another is SNuPE.

In addition to measuring the degree of imprinting when an imprinted polymorphism is present in a gene, it is possible to assess the degree of LOI in a particular gene even when an imprinted polymorphism is not present in that gene. For example, imprinting can be assessed by the degree of methylation of CpG islands in or near an imprinted gene (e.g., Barletta, Cancer Research, op. cit). In addition, imprinting can be assessed by changes in DNA replication timing asynchrony, e.g. White L M, Rogan P K, Nicholls R D, Wu B L, Korf B. Knoll J H, Allele-specific replication of 15q11-q13 loci: a diagnostic test for detection of uniparental disomy. *American Journal of Human Genetics*. 59:423-30, 1996.

On the other hand, certain techniques are more conveniently used when there is a polymorphism in the two alleles of the gene or genes for which the presence or absence of LOI is being measured. For example, RT-PCR, followed by gel electrophoresis to distinguish length polymorphisms, or RT-PCR followed by restriction enzyme digestion, or by automated DNA sequencing, or by single strand conformational polymorphism (SSCP) analysis, or denaturing gradient gel electrophoresis, etc.; or, completely DNA based methods that exploit, for example DNA methylation, which require no RT step, to convert RNA to cDNA prior to PCR).

Once the degree of LOI has been measured for the gene or genes in question, the risk of having cancer is then assessed by comparing the degree of LOI for that gene or genes is to a known relationship between the degree of LOI and the probability of the presence of the particular type of cancer or other disease. The relationship between the degree of LOI and the probability of the presence of a particular type of cancer may be determined for any combination of a normally imprinted gene or genes and a particular type of cancer by determining.

When the degree of LOI is measured, such as the degree of IGF2 hypomethylation, the measured degree of LOI is compared to a known relationship between the degree of LOI and the probability of contracting the particular type of cancer. The relationship between the degree of LOI and the probability of contracting a particular type of cancer may be determined by one of ordinary skill in the art for any combination of a normally imprinted gene or genes and a particular type of cancer by determining the degree of LOI in a statistically meaningful number of tissue samples obtained from patients with cancer, and determining the degree of LOI in a statistically meaningful number of tissue samples obtained from patients without cancer, and then calculating an odds ratio as a function of the degree of LOI.

It should also be understood that measuring the degree of LOI, can be carried out by comparing the degree of LOI against one or more predetermined threshold values, such that, if the degree of LOI is below a given threshold value, which can be manifested in a regular methylation pattern, then the subject is assigned to a low risk population for having cancer, contracting cancer, and/or having replication error repair defects. Alternatively, the analytical technique may be designed not to yield an explicit numerical value for the degree of LOI, but instead yield only a first type of signal when the degree of LOI is below a threshold value and/or a second type of signal when the degree of LOI is below a threshold value. It is also possible to carry out the present methods by means of a test in which the degree of LOI is signaled by means of a non-numeric spectrum such as a range of colors encountered with litmus paper.

In another aspect, the present invention includes kits that are useful for carrying out the methods of the present invention. The components contained in the kit depend on a number of factors, including: the condition, state, or phenomenon relied on to detect LOI or measure the degree of LOI, the particular analytical technique used to detect LOI or measure the degree of LOI, and the gene or genes for which LOI is being detected or the degree of LOI is being measured.

Accordingly, the present invention provides a kit for determining a methylation status of a differentially methylated region (DMR) of IGF2 corresponding to SEQ ID NO:1 or a polymorphism thereof. The kit includes an oligonucleotide probe, primer, or primer pair, or combination thereof for carrying out a method for detecting hypomethylation, as discussed above. For example, the probe, primer, or primer pair, can be capable of selectively hybridizing to the DMR either with or without prior bisulfite treatment of the DMR. The kit can further include one or more detectable labels.

The kit can also include a plurality of oligonucleotide probes, primers, or primer pairs, or combinations thereof, capable of selectively hybridizing to the DMR with or without prior bisulfite treatment of the DMR. The kit can include an oligonucleotide primer pair that hybridizes under stringent conditions to all or a portion of the DMR only after bisulfite treatment. The kit can include instructions on using kit components to identify an increased risk of developing cancer. In certain embodiments the instructions relate to subjects of the general population.

When LOI is detected by relying on the degree of methylation of the genomic DNA associated with the gene(s) for which LOI is being detected or the degree of LOI is being measured using FISH, the kit will typically contain one or more probes which can identify a specific imprinted gene or group of genes. Typically, such probes will be nucleic acids or monoclonal antibodies and will be linked to, for example, a fluorescent label.

In the case of detecting LOI by relying on the differential rates of transcription of two polymorphic alleles, the kit can include:

(i) means for the amplification of the mRNAs corresponding to the two polymorphic alleles of the gene in question. Examples of such means include suitable DNA primers for the PCR amplification of the mRNAs corresponding to the two polymorphic alleles of the gene in question. Specific examples of such means include any pair of DNA primers which will anneal to and amplify any gene which is normally imprinted and in which a polymorphism is present.

According to the present invention, the kit may further include:

(ii) means for identifying the products of the amplification of the mRNAs corresponding to the two polymorphic alleles of the gene in question. Such means include, but are not limited to, a restriction enzyme which specifically cleaves one of the products of the amplification of the mRNAs corresponding to the two polymorphic alleles of the gene in question. Specific examples of such enzymes include, but are not limited to, Apa I in the case of the IGF2 gene.

When the degree of LOI is measured by relying on the differential rates of transcription of two polymorphic alleles, the kit may comprise:

(i) means for the linear amplification of the mRNAs corresponding to the two polymorphic alleles of the gene in question. Examples of such means include a sufficient quantity of suitable DNA primers for the PCR amplification of the mRNAs corresponding to the two polymorphic alleles of the gene in question, such that the PCR amplification may be carried out without exhausting the primers and linear amplification achieved. Specific examples of such means includes any pair primers for any gene which is normally imprinted.

According to the present invention, the kit can further include:

(ii) means for identifying the products of the amplification of the mRNAs corresponding to the two polymorphic alleles of the gene in question. Such means include a restriction enzyme which specifically cleaves one of the products of the amplification of the mRNAs corresponding to the two polymorphic alleles of the gene in question.

When detecting LOI or measuring the degree of LOI by ASISH, the kit will typically contain one or more probes which can identify and distinguish between the RNA associated with the two alleles. Typically, such probes will be nucleic acids that are specific for each allele, and are used either sequentially or together using different fluorescent labels for each allele.

When detecting LOI or measuring the degree of LOI by assessing the relative translation of two alleles, the kit may contain antibodies that distinguish the protein product of the two alleles.

The following example is intended to illustrate but not limit the invention.

EXAMPLE 1

Association of Loss of Imprinting and Colorectal Neoplasia

This example illustrates that LOI in normal tissue is associated with either a family history or personal history of colorectal neoplasia.

Materials & Methods

Study Population. Subjects were identified and recruited in the Johns Hopkins Outpatient Endoscopy Clinic and the Johns Hopkins Greenspring Endoscopy Unit. Eligible subject were those individuals who were having a colonoscopy for any medical indication, who were 18 years of age or older and who had physician approval. Written informed consent was obtained from all subjects. Clinical, demographic, family history and exposure information were obtained with the use of validated questionnaires. The protocol was approved by the Johns Hopkins Joint Committee on Clinical Investigation.

Collection of Research Materials. Colon tissues were collected from patients who underwent a colonoscopy. Ninety-seven percent of patients agreed to participate. Colonoscopic examinations were performed with a standard Olympus colonoscope by several endoscopists. Up to 8 mucosal punch biopsies were obtained from proximal and distal colon using routine biopsy forceps. The tissues were immediately frozen in liquid nitrogen and stored at −135° C. Lymphocytes were separated from blood (20 ml) from every patient with Accuspin tubes (Sigma/Aldrich, St. Louis, Mo.) using Ficoll-Paque Plus (Amersham Pharmacia Biotech, Pisacataway, N.J.) and centrifuged at 400 g at room temperature for 30 minutes. The lymphocyte layer was collected and washed once with PBS. The isolated lymphocyte pellets were immediately stored at −135° C. until the assays were performed.

DNA and RNA Preparation. DNA extraction was performed as previously described (Cui, H., et al., *Nat. Med.* 4, 1276-1280 (1998), incorporated in its entirety herein by reference). RNA was extracted from frozen mucosal punch biopsies and lymphocytes with the RNeasy Mini Kit (Qiagen, Valencia, Calif.) shortly before RT. Each RNA sample was quantified by spectrophotometry and agarose gel electrophoresis, treated with 10µ RNase inhibitor (Invitrogen, Carlsbad, Calif.) and used immediately.

Quantitative Analysis of IGF2 Imprinting Status. Reverse transcription was performed with freshly extracted RNA samples, which had been treated with DNase I to remove any DNA contamination as previously described (Cui, H., et al., *Nat. Med.* 4, 1276-1280 (1998)). Quantitative analysis of IGF2 imprinting status was performed by Hot-stop PCR (Uejima, H., et al., *Nat. Genet.* 25, 375-376 (2000), incorporated herein in its entirety, by reference). All reactions were done in duplicate with presence and absence of reverse transcriptase on identical RNA sample to exclude any possibility of DNA contamination.

Detection of DNA Methylation. The IGF2 DMR is located on positions −566 to −311 relative to IGF2 exon 3 (corresponding to positions 661 to 916 of GenBank accession no. Y13633). Analysis of methylation was performed by bisulfite genomic sequencing by analyzing positions 87, 90, and 106 of the IFG2 DMR (SEQ ID NO:1). Genomic DNA was treated with bisulfite, as follows: Sodium hydroxide was added to genomic DNA to a final concentration of 0.3M and incubated at 37° C. for 20 min to denature the genomic DNA. A sodium metabisulfite solution is added to the denatured DNA to a concentration of about 2M sodium metabisulfite (EM Sience) and 10 mM hydroquinone (EM Science), pH 7.0, and the DNA in the sodium metabisulfite solution is incubated at 55° C. in the dark for about 12-16 hrs. Treated DNA was purified with the QIAquick PCR purification kit according manufacturer's protocol. The purified DNA was exposed to about ⅒ volume of 3M NaOH and incubated at 37° C. for 20 min. Five molar $NH_4OAC$ to a final 3M concentration and kept at room temperature for 5 min to neutralize DNA. Five μg yeast RNA and 3× volume of pure ethanol and were added to the neutralized DNA, and the solutions were kept at −80° C. for 30 min and then centrifuged to precipitate DNA. The DNA was then washed with 70% ethanol, dissolved in TE (pH 7.2), and stored at −20° C. for PCR.0

PCR was performed as follows: Treated DNA was amplified by PCR, using primers 5'-GGTGAGGATGGGTTTTTGTT-3' (SEQ ID NO:2) and 5'-CTACTCTCCCAACCTCCCTAA-3' (SEQ ID NO:3), annealing at 55° C., followed by nested PCR using primers 5'-ATTGGGGGTGGAGGGTGTAT-3' (SEQ ID NO:4) and 5'-TCTATTACACCCTAAACCCAA-3' (SEQ ID NO:5), annealing at 52° C.

PCR products were purified on 2% agarose gels for direct sequencing as described above. The annealing temperature was 55° C. For sequencing individual clones, the PCR products were subcloned into a TA Cloning vector (Invitrogen, Carlsbad, Calif.) according to the manufacturer's instructions, and 15-20 clones were selected for sequencing.

All of the PCR products were purified using the QIAEX II gel extraction kit (Qiagen) and directly sequenced with an ABI Prism 377 DNA sequencer using the BigDye Terminator Cycle Sequencing kit following the manufacturer's protocol (PE Applied Biosystems, Foster City, Calif.) (See Cui et al., 61:4947 (2001), incorporated herein in its entirety, by reference.

Statistical Analysis. Hypothesis testing was performed with a combination of chi-square and Fisher exact t-tests as appropriate. Multiple logistic regression models were constructed for the association of the independent covariates with LOI, and for the association of LOI with colorectal neoplasia and family history of cancer. Kappa statistics was used to determine agreement beyond chance. Statistical analysis was performed using STATA 7.0 software (Stata Corp.).

Results

To ensure complete ascertainment of colorectal neoplasia, a cross-sectional analysis was performed of patients who provided clinical and family history information. Contemporaneous colonoscopic examination was performed with mucosal biopsy. For logistical purposes, patients were chosen that were selected for colonoscopic examination for clinical indications. For this reason, there was modest enrichment for a past history of colonic adenoma or cancer (13%, compared to 10% in the general U.S. population of this age).

Four hundred and twenty one patients agreed to participate between 1999 and 2001. 191 patients were informative for either an APAI or CA repeat polymorphism within exon 9 of IGF2 allowing analysis of imprinting status. In addition to both proximal and distal colonic mucosal specimens, PBL for RNA and DNA analysis, a family and personal history of neoplasia, environmental exposures, medications, and dietary information was obtained.

First the relationship between LOI and age was examined. It has been suggested previously that altered IGF2 methylation is age-related, suggesting that epigenetic abnormalities are acquired over time (Issa, J. P., et al., *Proc. Natl. Acad. Sci. U.S.A.* 93, 11757-11762 (1996)). However, no relationship between LOI in PBL and age was found (Table 1). There were also no significant differences by sex or race (Table 1). Next the relationship between LOI and family history was analyzed. The odds of LOI in PBL were 4.4 times greater in patients with a positive family history of CRC compared to their counterparts with a negative family history (p=0.003; Table 1).

The relationship between LOI and colorectal neoplasia in the patient was next evaluated. The odds of LOI in PBL were 4.4 times greater in patients with past or present colorectal neoplasia (adenomatous polyps or cancer) than their counterparts without neoplasia (p=0.002; Table 1), indicating a strong association between LOI and colorectal neoplasia. Even when patients with a positive family history were excluded from the analysis, the odds of LOI in PBL these odds were 4.7 times greater (95% CI 1.29-17.3, p=0.01).

The accepted model for colorectal carcinogenesis is that cancers progress from adenomas (E. R. Fearon and B. Vogelstein, *Cell* 61, 759-767 (1990)). Consequently when stratified, the odds of LOI in PBL were 4.1 times greater in patients with past or present adenomas but no CRC, compared to patients with no past or present neoplasia (p=0.016; Table 1), and they were 34.4-fold greater in patients with past or present CRC than in those without colorectal neoplasia (p<0.0001; Table 1). These data strongly suggest that LOI is associated with both initiation and progression of colorectal neoplasia.

TABLE 1

Association of loss of imprinting (LOI) of IGF2 in peripheral blood lymphocytes with family history of colon cancer and with present or past colonic neoplasia in the patient.

| | Imprinting | | Unadjusted odds ratio | | | Adjusted odds ratio* | | |
|---|---|---|---|---|---|---|---|---|
| | Normal | LOI | | | | | | |
| | N (%) | N (%) | P value | OR | 95% CI | P value | OR | 95% CI |
| Age (± SD) | 58.7 ± 12.8 | 59.9 ± 9.7 | 0.64 | 1.00 | 0.97-1.04 | 0.35 | 1.02 | 0.97-1.07 |
| Sex | | | | | | | | |
| Women | 72 (85.7) | 12 (14.3) | | | | | | |
| Men | 75 (86.2) | 12 (13.8) | 0.93 | 0.96 | 0.41-2.28 | 0.70 | 1.21 | 0.45-3.23 |

TABLE 1-continued

Association of loss of imprinting (LOI) of IGF2 in peripheral blood lymphocytes with family history of colon cancer and with present or past colonic neoplasia in the patient.

|  | Imprinting | | Unadjusted odds ratio | | | Adjusted odds ratio* | | |
|---|---|---|---|---|---|---|---|---|
|  | Normal | LOI | | | | | | |
|  | N (%) | N (%) | P value | OR | 95% CI | P value | OR | 95% CI |
| Race |  |  |  |  |  |  |  |  |
| White | 129 (86.0) | 21 (14.0) |  |  |  |  |  |  |
| Black | 18 (85.7) | 3 (14.3) | 0.97 | 1.02 | 0.28-3.78 | 0.55 | 0.62 | 0.13-2.96 |
| Family history |  |  |  |  |  |  |  |  |
| No | 111 (91.0) | 11 (9.0) |  |  |  |  |  |  |
| Yes | 36 (73.4) | 13 (26.5) | 0.003 | 3.64 | 1.5-8.84 | 0.004 | 4.41 | 1.62-12.0 |
| Colonic Neoplasia |  |  |  |  |  |  |  |  |
| No | 99 (93.4) | 7 (6.6) |  |  |  |  |  |  |
| Yes | 48 (73.8) | 17 (26.2) | 0.001 | 5.01 | 1.94-12.89 | 0.002 | 4.37 | 1.74-11.0 |
| Adenomas | 44 (78.6) | 12 (21.4) | 0.008 | 3.85 | 1.42-10.5 | 0.016 | 4.10 | 1.30-12.8 |
| CRC | 4 (44.4) | 5 (55.6) | <0.0001 | 17.67 | 3.85-81.0 | <0.0001 | 34.4 | 6.10-194 |

*Hypothesis testing performed with multiple logistic regression adjusted for age, gender, race, family history, and physical activity; OR, odds ratio; 95% CI, 95% confidence interva The relationship between LOI in PBL and LOI in the colon was determined in patients from whom informative samples sufficient for imprinting analysis could be obtained in both tissues. All of the patients with LOI in PBL also showed LOI in normal colon (Table 2 and data not shown). In the remainder LOI was limited to the colon (Table 2), and in these patients it was present variably in proximal or distal colonic mucosa (data not shown). Thus, LOI either was a generalized defect affecting both blood and colon, or a focal abnormality within one or more samples within the colon. In the latter group, no statistically significant association with family or personal history of colorectal neoplasia was found.

TABLE 2

Concordance of imprinting status between colonic mucosa and blood*

| BLOOD | COLON | |
|---|---|---|
|  | Normal | LOI |
| Normal | 123 | 21 |
| LOI | 0 | 24 |

*Kappa statistic 88.0%, p value < 0.0001

Figure 2B:
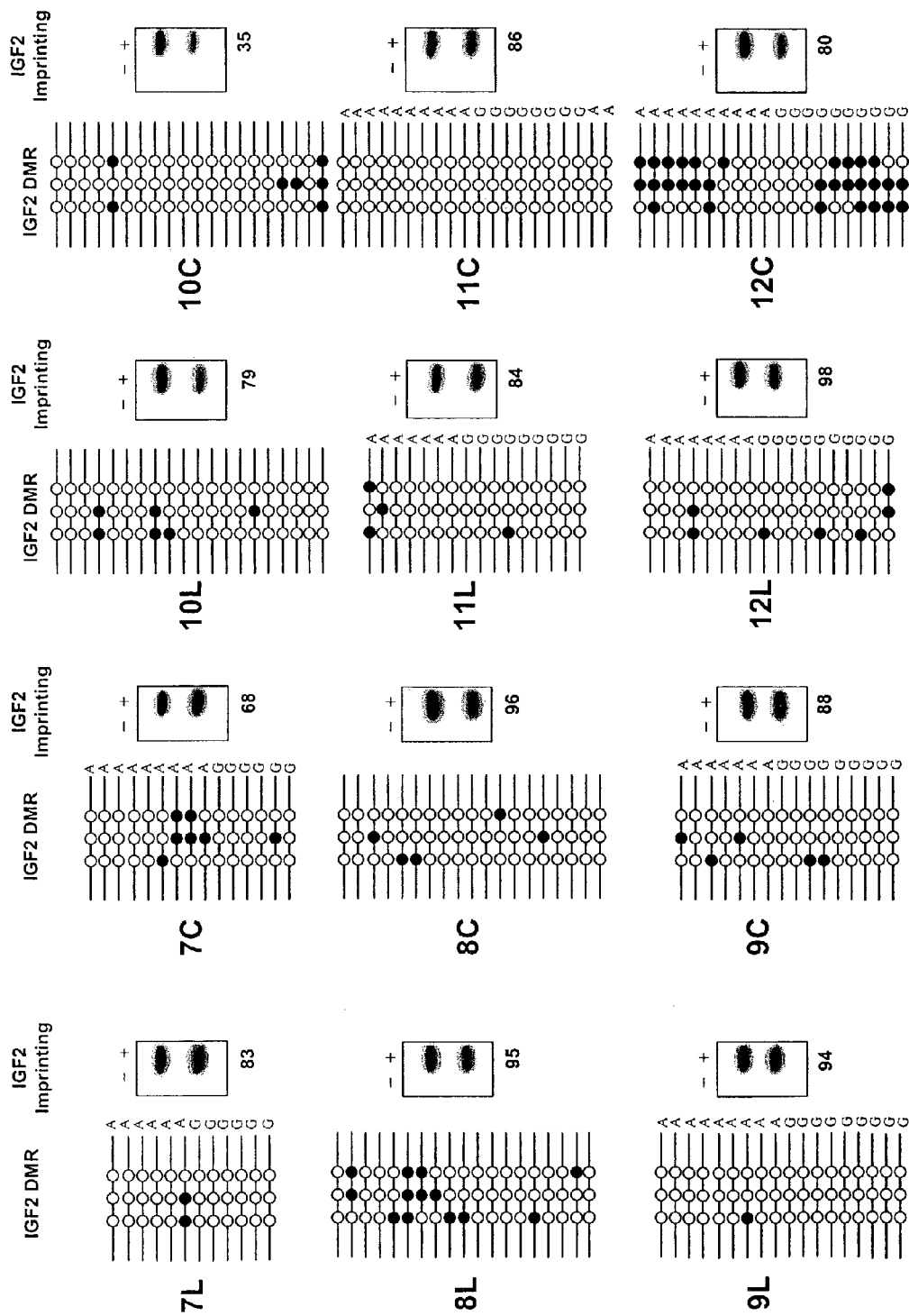

It was next determined whether a method of the present invention can be performed using DNA rather than RNA. SEQ ID NO:1 provides a differentially methylated region (DMR) within IGF2 that shows hypomethylation in CRC with LOI (Cui H. et al., *Cancer Res.* 62, 6442-6446 (2002), incorporated herein in its entirety by reference). In order to determine whether a hypomethylation defect occurs in PBL and colon of patients without known neoplasia, we examined 24 samples, 12 from normal tissues (6 PBL, 6 matched normal colonic mucosa) with normal imprinting, and 12 from normal tissues (6 PBL, 6 matched normal colonic mucosa) with LOI. In all 12 tissues with normal imprinting, IGF2 showed a normal pattern of half-methylation (FIG. 2A). In contrast, in 11 of 12 samples from normal tissue with LOI, IGF2 showed hypomethylation of the IGF2 DMR; in the other sample, IGF2 showed partial methylation of both alleles but was nevertheless abnormal (FIG. 2B). The significance of hypomethylation between normal tissues with and without LOI was p<0.0001 (Fisher's exact test). In contrast, H19 showed hypomethylation in all cases, regardless of imprinting status (data not shown). Thus, aberrant IGF2 methylation is linked to LOI in normal colon and lymphocytes, just as it is in CRC.

In summary, a strong and significant association of LOI with family history, and with present or past personal history of colorectal neoplasia was identified using methods of the present invention. When present in PBL, LOI appears to be a systemic abnormality, since it was always also present in both proximal and distal colon. It cannot be concluded currently that the abnormality is present in the germline, as it is epigenetic and might be acquired postnatally. This abnormality is common, present in 14% of the patients studied, which by design may be mildly enriched for CRC. Nevertheless, a 10% frequency of LOI in PBL in the general population has previously been observed (Cui, H., et al., *Nat. Med.* 4, 1276-1280 (1998); Sakatani, T., et al., *Biochem. Biophys. Res. Commun.* 283, 1124-1130 (2001)).

This epigenetic abnormality was present at both the RNA and DNA level. Eleven of 12 tissues with LOI showed hypomethylation of IGF2, and all 12 tissues with normal imprinting showed normal methylation of IGF2. The methylation assay may be improved, as the entire IGF2 DMR has not yet been examined by bisulfite sequencing. There may be a critical core sequence involved, with nearby sequences showing variable alteration, as found near the H19 and other DMRs in development (Davis, T. L., et al., *Hum. Mol. Genet* 9, 2885-2894 (2000)).

The odds ratio for colorectal cancer of LOI (34.4) is higher than seen for mutation of the mismatch repair genes in HNPCC (H. T. Lynch and J. F. Lynch, *Semin. Surg. Oncol.* 18, 305-313 (2000)), which confers an 80% lifetime risk of CRC (H. T. Lynch and A. de la Chapelle, *J. Med. Genet.* 36, 801-818 (1999)). In contrast, the I1307K mutation of APC confers only a two-fold increased risk of colorectal cancer (Laken S. J., et al., *Nat. Genet.* 17, 79-83 (1997)). Furthermore, the prevalence of LOI, 10%, is at least 10-fold higher than all known CRC-predisposing genetic mutations in the population combined (Samowitz, W. S., et al., *Gastroenterology* 121, 830-838 (2001); and Percesepe, A., et al., *J. Clin. Oncol.* 19, 3944-3950 (2001)). Consequently, conventional genetic mutation screening for cancer risk has been targeted at defined populations with a strong family history, and not for screening and surveillance in the general population. In contrast an LOI blood test might be of value for population screening.

Although the invention has been described with reference to the above example, it will be understood that modifications and variations are encompassed within the spirit and scope of the invention. Accordingly, the invention is limited only by the following claims.

What is claimed is:

1. A method for prognosing colorectal cancer risk of a human subject, comprising:
   a) obtaining a first biological sample from the subject, wherein the first biological sample is a blood sample or a colorectal tissue sample;
   b) analyzing the first biological sample from the subject for biallelic hypomethylation of a differentially methylated region of IGF2 having the sequence of SEQ ID NO:1; and
   c) detecting biallelic hypomethylation at positions 87, 90, and 106 of SEQ ID NO:1, wherein the biallelic hypomethylation is indicative of an increased risk of developing colorectal cancer, thereby prognosing colorectal cancer risk of the subject.

2. The method of claim 1, further comprising:
   d) obtaining a second biological sample from the subject, wherein the second biological sample is a blood sample or a colorectal tissue sample;
   e) analyzing the second biological sample for biallelic hypomethylation of a differentially methylated region of IGF2 having the sequence of SEQ ID NO:1; and
   f) detecting biallelic hypomethylation at positions 87, 90, and 106 of SEQ ID NO:1, wherein biallelic hypomethylation at positions 87, 90, and 106 of SEQ ID NO:1 in the second biological sample is indicative of an increased risk of developing colorectal cancer.

3. The method of claim 2, wherein the method further comprises performing routine colonoscopy or gastrointestinal endoscopy of the subject.

4. The method of claim 1, wherein the method comprises analyzing genomic DNA from the first biological sample for biallelic hypomethylation of a differentially methylated region of IGF2.

* * * * *

UNITED STATES PATENT AND TRADEMARK OFFICE
CERTIFICATE OF CORRECTION

| | | |
|---|---|---|
| PATENT NO. | : 7,611,870 B2 | Page 1 of 1 |
| APPLICATION NO. | : 10/336552 | |
| DATED | : November 3, 2009 | |
| INVENTOR(S) | : Andrew P. Feinberg | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 803 days.

Signed and Sealed this

Twelfth Day of October, 2010

David J. Kappos
*Director of the United States Patent and Trademark Office*